United States Patent
Hamel

(12) 
(10) Patent No.: US 6,361,516 B1
(45) Date of Patent: Mar. 26, 2002

(54) POSTERIOR ANKLE SPLINT SHAPER

(76) Inventor: Christopher Ronald Hamel, 10722 48th St., East Edgewood, WA (US) 98372

( * ) Notice: Subject to any disclaimer, the term of this patent is extended or adjusted under 35 U.S.C. 154(b) by 0 days.

(21) Appl. No.: 09/710,749

(22) Filed: Nov. 9, 2000

(51) Int. Cl.[7] .................................................. A61F 5/00
(52) U.S. Cl. ........................ 602/27; 128/882; 482/124; 482/125
(58) Field of Search ................................ 128/846, 869, 128/882; 602/32–40; 482/121, 124, 125

(56) References Cited

U.S. PATENT DOCUMENTS

| | | | |
|---|---|---|---|
| 1,734,238 A | * 11/1929 | Sweeney | ..................... 482/124 |
| 4,505,269 A | 3/1985 | Davies et al. | |
| 4,628,945 A | 12/1986 | Johnson, Jr. | |
| 4,966,134 A | 10/1990 | Brewer | |
| 4,977,891 A | 12/1990 | Grim | |
| 5,000,195 A | 3/1991 | Neal | |
| 5,263,916 A | * 11/1993 | Bobich | ....................... 482/124 |
| 5,605,535 A | 2/1997 | Lepage | |
| 5,688,213 A | * 11/1997 | Recker | ....................... 482/125 |
| 5,820,534 A | * 10/1998 | Vadher | ....................... 482/124 |
| 5,957,871 A | 9/1999 | Darcey | |
| 5,980,747 A | 11/1999 | Darcey | |
| 6,022,331 A | 2/2000 | Darcey | |

* cited by examiner

*Primary Examiner*—Michael A. Brown
(74) *Attorney, Agent, or Firm*—John D. Gugliotta; P. Jeff Martin

(57) ABSTRACT

A posterior ankle splint shaper apparatus is provided forming a shoe having an upper surface opposite a lower surface and including a pair of ankle straps, a pair of foot straps, and a pair of linearly elongated maintenance straps.

11 Claims, 3 Drawing Sheets

POSTERIOR ANKLE SPLINT SHAPER

RELATED APPLICATIONS

The present invention was first described in Disclosure Document No. 470,803, filed on Mar. 13, 2000. There are no previously filed, nor currently any co-pending applications, anywhere in the world.

BACKGROUND OF THE INVENTION

1. Field of the Invention

The present invention relates generally to splints, braces, bandages and the like and, more particularly, to a device and method to immobilize a splinted limb at the appropriate angle during casting.

2. Description of the Related Art

As is well-known in the art, the use of fiberglass casts or splints have just about replaced the use of the old plaster-type casts. The fiberglass version is lighter, stronger, less susceptible to damage from physical abuse and damage from water. However, there are still application requirements which must be followed when applying a fiberglass splint. Perhaps the most important of these is the requirement that the bone structure remain in alignment while the fiberglass is hardening. This is very important especially when applying splints to ankle injuries. In the past, medical personnel such as nurses have had to hold the foot and ankle in position while the fiberglass hardens. This practice not only occupies the time of the nurse that perhaps could be put to better use elsewhere, but it also comprises the placement of the ankle which should be kept at an exact 90° for maximum healing benefit.

A search of the prior art did not disclose any patents that read directly on the claims of the instant invention; however, the following references were considered related.

The following patents disclose a custom-fitted ankle splint.

U.S. Pat. No. 6,022,331 issued in the name of Darcey
U.S. Pat. No. 5,980,474 issued in the name of Darcey
U.S. Pat. No. 5,957,871 issued in the name of Darcey
The following patents describe an ankle splint.
U.S. Pat. No. 5,605,535 issued in the name of Lepage
U.S. Pat. No. 5,000,195 issued in the name of Neal
U.S. Pat. No. 4,966,134 issued in the name of Brewer
U.S. Pat. No. 4,505,269 issued in the name of Davies et al.
U.S. Pat. No. 4,977,891 issued in the name of Grim disclose a variable support ankle brace.
U.S. Pat. No. 4,628,945 issued in the name of Johnson, Jr. describe an inflatable ankle brace with a porous compressible filler.

Consequently, there exists a need for a means by which fiberglass ankle casts or splints can be kept at a specific angular relationship while the fiberglass hardens or dries.

SUMMARY OF THE INVENTION

Therefore, it is an object of the invention to provide for a device and method to immobilize a splinted limb at the appropriate angle during casting.

It is a feature of the present invention to provide a splint forming aid. Once a fiberglass or plaster splint is applied, this device is put on to hold the splint in a 90 degree angle so the material can set up and harden. This shaper replaces a medical person that would normally stand there and flex the patient's foot in the 90 degree angle. The splinted foot is placed into a stiff sandal then VELCRO(™) straps, which are attached to the sandal or wrapped around it, are pulled by the patient until the foot is in a 90 degree position. The doctor would most likely set this up and instruct the patient how far to pull the straps. This is held for probably 10–15 minutes until the fiberglass is hardened in place.

The present invention is designed to free up nursing personnel to perform other tasks, who are conventionally used to hold the cast in position while it hardens. After medical procedures have been applied and the fiberglass cast applied, the invention is then placed over the cast and secured with the use of nylon straps to the patient's foot area. Next, two large straps, connected to the invention at the toe area, are pulled back and secured to one another behind the patient's calf area of the leg using hook and loop fastener such as VELCRO(™). Such a procedure allows the foot to be held at a 90° angle with respect to the patient's leg. This action then allows the fiberglass cast to harden in a position that will result in the most health benefit for the user.

The use of posterior ankle splint shaper results in more accurate setting of fiberglass ankle splints or casts while concurrently freeing up medical personnel to perform other tasks.

Another advantage of the present invention is that it holds fiberglass ankle splints in position until they harden.

Another advantage of the present invention is that it provides for more accurate setting.

Yet another advantage of the present invention is that it frees medical personnel to perform other tasks.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
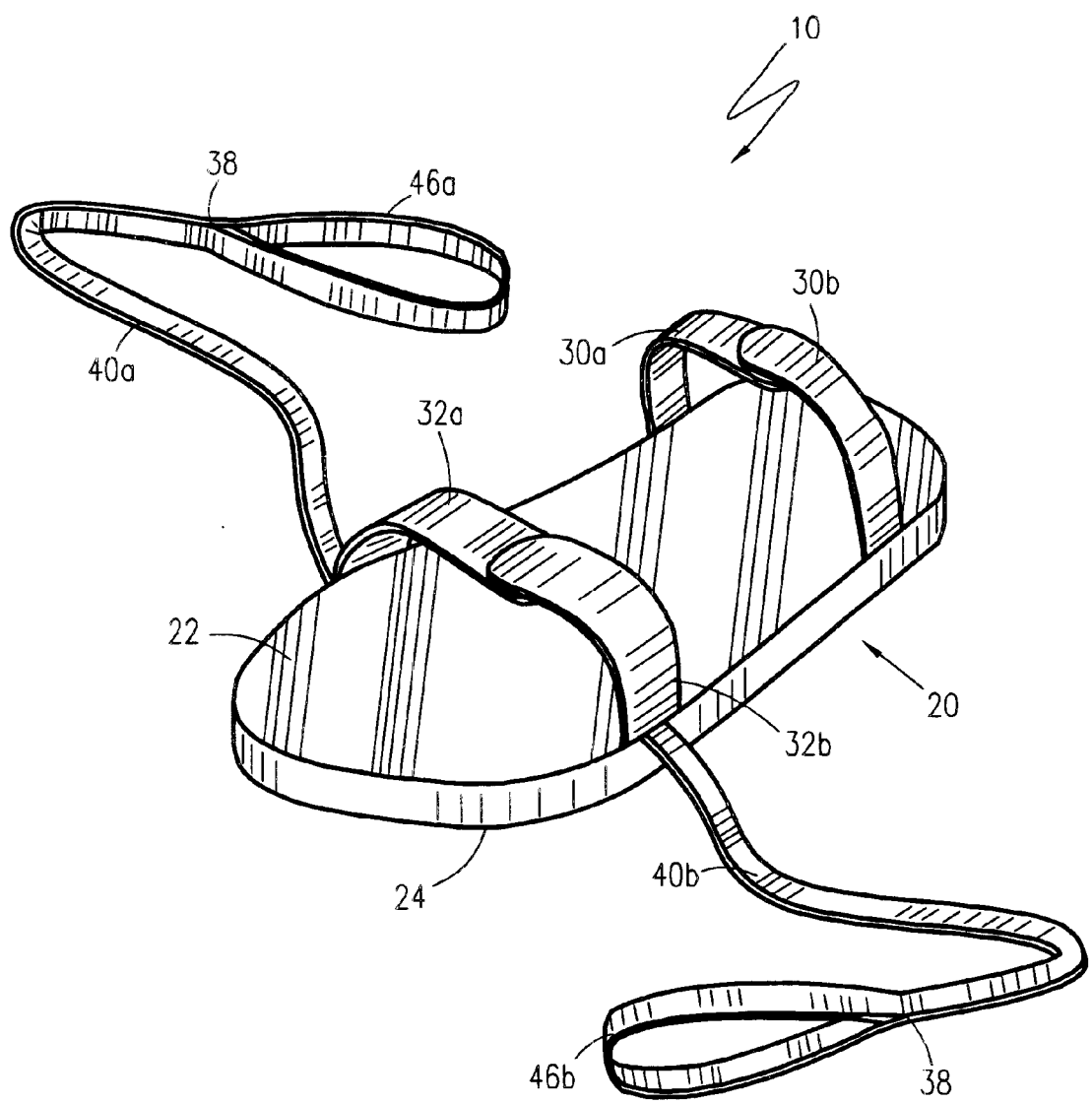
FIG. 1 is a perspective view of a posterior ankle splint shaper according to the preferred embodiment of the present invention.
Figure 2:
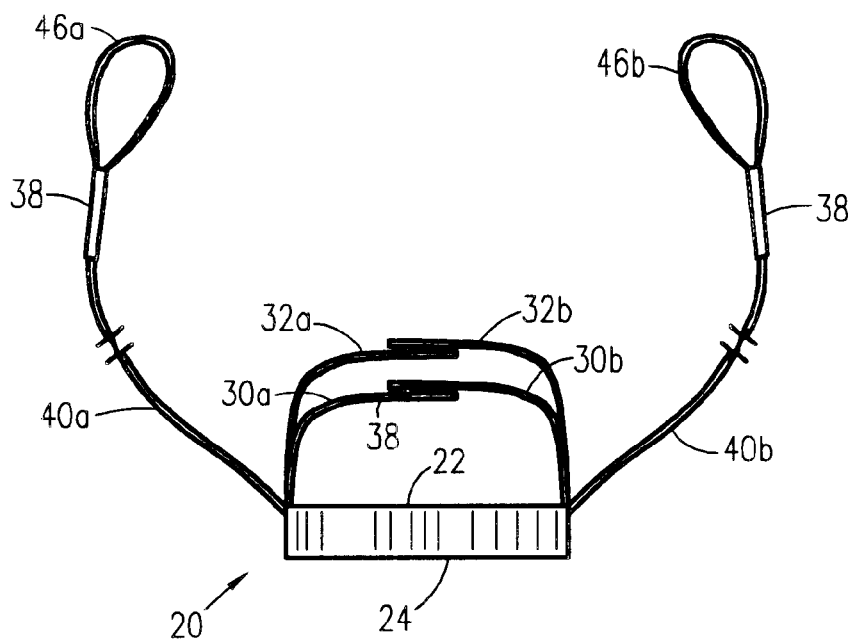
FIG. 2 is a front end elevational view thereof.
Figure 3:
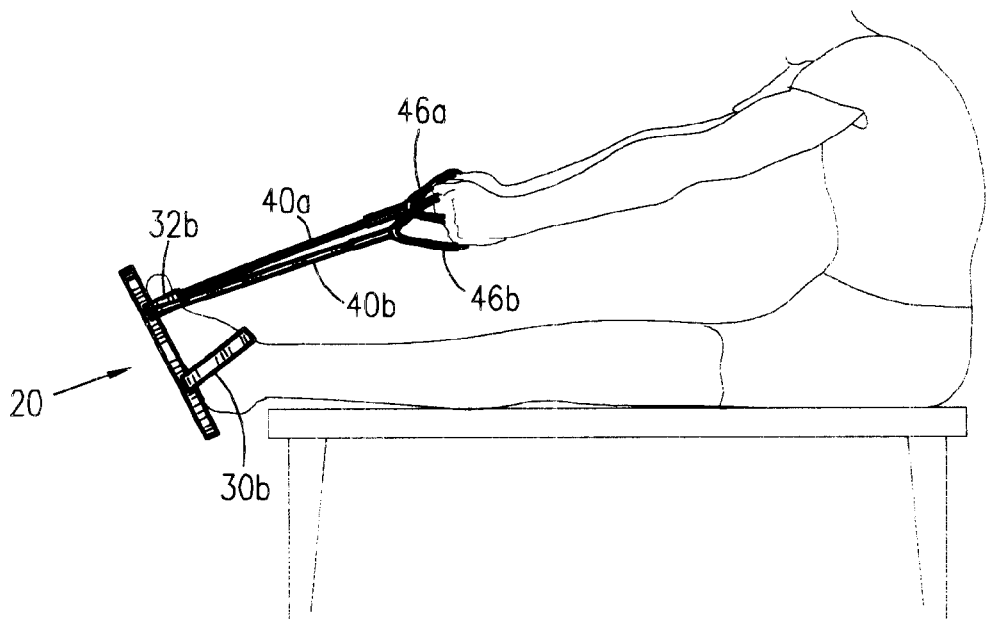
FIG. 3 is a side view of the present invention according to the preferred embodiment shown in-use.
Figure 4:
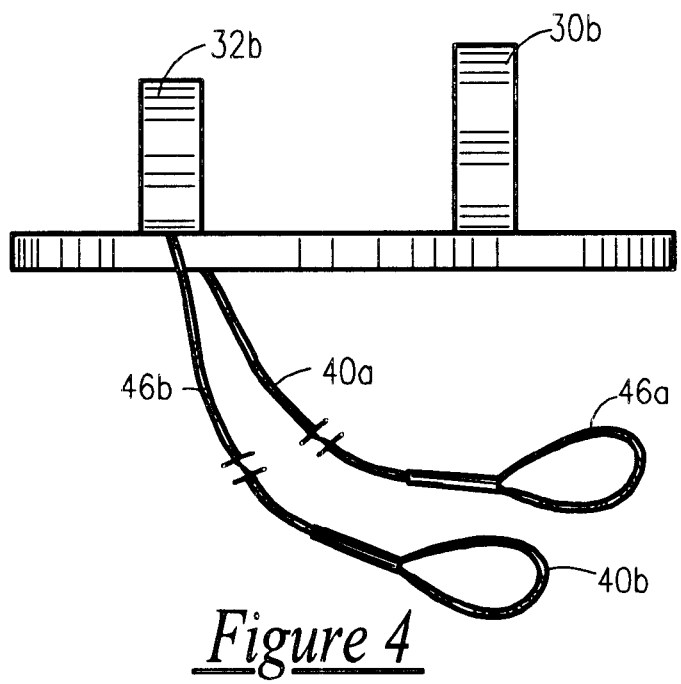
FIG. 4 is a side elevational view of the present invention according to the preferred embodiment.

Referring now to FIGS. 1–4, a posterior ankle splint shaper apparatus 10 is shown, according to the present invention, comprised of a shoe 20 having an upper surface 22 opposite a lower surface 24 which includes a pair of ankle straps 30a, 30b, a pair of foot straps 32a, 32b, and a pair of linearly elongated maintenance straps 40a, 40b for immobilizing a splinted limb at an appropriate angle during fiberglass or plaster casting.

The shoe 20 is of a linearly elongated rectangular configuration resembling a sole of a conventional shoe and is constructed of a substantially-rigid material preferably formed of an injection molded high impact thermoplastic such as high impact polypropylene or polyurethane. The shoe 20 further having dimensions so as to ideally fit an average adult male foot.

It is envisioned that various sizes of the posterior ankle splint shaper apparatus 10 may be required so as to accommodate various foot sizes of children and females.

Posteriorly attached with respect to a patient's ankle to opposing portions of the shoe 20, a pair of ankle straps 30a, 30b for removably securing a patient's heel firmly against the upper surface 22 of the shoe 20. Ends of each of the ankle straps 30a, 30b are secured in position in an overlapping manner with the use of VELCRO(™) material 38. The securing means disclosed for securing the ends of the ankle straps 30a, 30b is only meant as a suggestion and is in no way limiting. The ankle straps 30a, 30b are constructed of a material such as nylon, vinyl, or the like.

Attached above the ankle straps 30a, 30b to opposing portions of the shoe 20 are a pair of foot straps 32a, 32b for removably securing a patient's foot firmly against the upper surface 22 of the shoe 20. Ends of each of the foot straps 32a, 32b are secured in position in an overlapping manner with the use of VELCRO(™) material. The foot straps 32a, 32b are constructed of a material such as nylon, vinyl, or the like.

Figure 5:
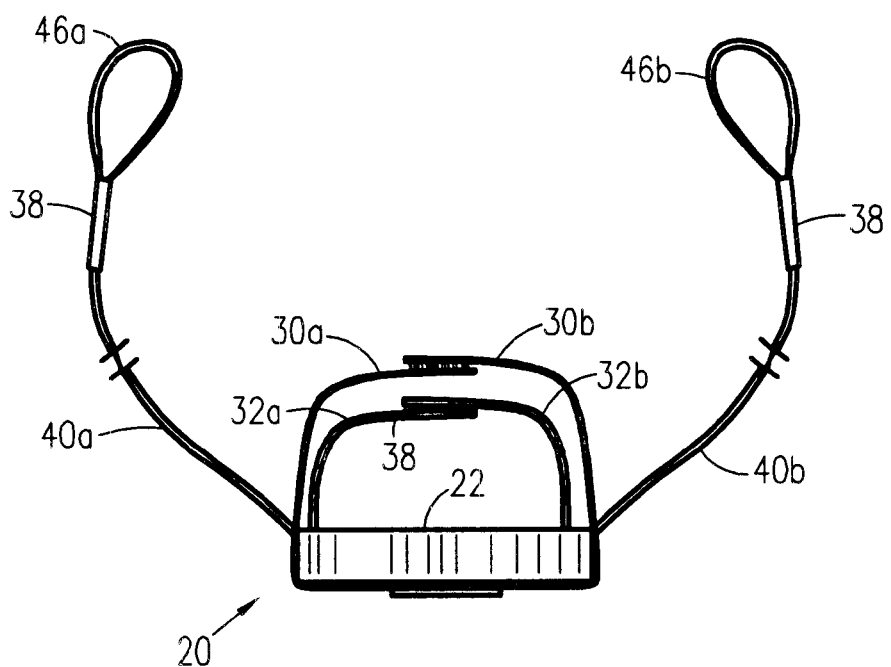
FIG. 5 is a front end elevational view according to an alternate embodiment of the present invention.

Referring now to FIG. 5, an alternate embodiment of the present invention is shown wherein both the ankle straps 30a, 30b and the foot straps 32a, 32b may each comprise a single length of suitable material such as nylon, vinyl, and the like for being tightly placed around the lower surface 24 of the shoe 20 and over the top portion of a patient's foot, thereby being secured there around using VELCRO(™) material 38 being secured at opposing ends of the ankle strap 30a, 30b and the foot strap 32a, 32b.

Referring now to FIGS. 1–4, shown attached near a toe area 44 to opposing portions of the shoe 20 is a pair of linearly elongated, elastic maintenance straps 40a, 40b. Each of the maintenance straps 40a, 40b are formed of a resilient, elastic rubber material having resilient properties permitting the maintenance straps 40a, 40b to be stretched within reasonable limits and returning to its natural configuration after releasing of tension. Each of the maintenance straps 40a, 40b further having a loop 46a, 46b formed at ends thereof so as to provide a grasping means for a patient. The patient pulls back on the elastic maintenance straps 40a, 40b in a protracted position, thereby in turn, pulling a splinted foot in a forward direction to an appropriate angle, i.e., 90° relative to the patient's leg.

In order to maintain the splintered foot at a chosen angle, ends below the loops 46a, 46b of each of the maintenance straps 40a, 40b are secured in position in an overlapping manner behind the patients knee near the calf area with the use of VELCRO(™) material 38, thereby providing a hands-free device for immobilizing a splinted limb during the period required for the hardening of a cast resulting in the most health benefit for the patient.

In the alternative, the patient may choose to maintain the splinted foot at an appropriate angle by simply pulling back and holding the loops 46a, 46b of the maintenance straps 40a, 40b with his hands rather than securing the ends of the maintenance straps 40a, 40b in an overlapping, secured position behind the patients knee near the calf area during the period required for the hardening of the cast.

Utilization by the patient of either securing the maintenance straps 40a, 40b in position in an overlapping manner behind the patient's knee, or simply pulling back on and holding the loops 46a, 46b will operate equally well for immobilizing a splinted limb at an appropriate angle.

The design and use of the posterior ankle splint shaper apparatus 10 results in more accurate setting of fiberglass ankle splints or casts while concurrently freeing up medical personnel to perform other tasks.

2. Operation of the Preferred Embodiment

To use the present invention, after medical procedures have been applied and the fiberglass or plaster cast has been applied, the posterior ankle splint shaper apparatus 10 is then placed over the cast and secured with the use of the ankle straps 30a, 30b and foot straps 32a, 32b to the patient's foot area. Next, the pair of maintenance straps 40a, 40b, which are attached near a toe area 44 to opposing portions of the shoe 20 and having loops 46a, 46b formed at ends thereof, are pulled back by the loops 46a, 46b and secured behind the patient's knee near the calf area using hook and loop fastener such as VELCRO(™). Such procedure allows the foot to be held at a 90° angle with respect to the patient's leg. This action then allows the fiberglass or plaster cast to harden in a position that will result in the most health benefit for the patient.

As designed, a device embodying the teachings of the present invention is easily applied. The foregoing description is included to illustrate the operation of the preferred embodiment and is not meant to limit the scope of the invention.

As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. A posterior ankle splint shaper apparatus comprising a shoe having an upper surface opposite a lower surface and including a pair of ankle straps, a pair of foot straps, and a pair of linearly elongated maintenance straps; wherein said ankle splint shaper is capable of immobilizing a splinted limb at an appropriate angle during casting, wherein said shoe is of a linearly elongated rectangular configuration and is constructed of a substantially-rigid material.

2. The posterior ankle splint shaper apparatus of claim 1, wherein said substantially-rigid material comprises an injection molded high impact thermoplastic.

3. The posterior ankle splint shaper apparatus of claim 1, wherein said ankle straps are posteriorly attached with respect to a patient's ankle to opposing portions of the shoe for removably securing a patient's heel firmly against an upper surface of said shoe.

4. The posterior ankle splint shaper apparatus of claim 3, wherein ends of each of said ankle straps are secured in position in an overlapping manner with the use of hook and loop fastener material.

5. The posterior ankle splint shaper apparatus of claim 4, wherein said ankle straps are constructed of nylon.

6. The posterior ankle splint shaper apparatus of claim 3, wherein said foot straps are attached above said ankle straps to opposing portions of said shoe for removably securing a patient's foot firmly against said upper surface of said shoe.

7. The posterior ankle splint shaper apparatus of claim 6, wherein ends of each of said foot strap is secured in position in an overlapping manner with the use of hook and loop fastener material.

8. The posterior ankle splint shaper apparatus of claim 7, wherein said foot straps are constructed of nylon.

9. The posterior ankle splint shaper apparatus of claim 8, wherein said maintenance straps are attached near a toe area to opposing portions of said shoe.

10. The posterior ankle splint shaper apparatus of claim 9, wherein each said maintenance strap is formed of a resilient, elastic rubber material having resilient properties permitting said maintenance straps to be stretched within reasonable limits and returning to its natural configuration after releasing of tension.

11. The posterior ankle splint shaper apparatus of claim 10, wherein each said maintenance strap further comprises a loop formed at ends thereof so as to provide a grasping means for a patient.

* * * * *